(12) United States Patent
Sullivan et al.

(10) Patent No.: US 6,650,936 B2
(45) Date of Patent: Nov. 18, 2003

(54) METHOD AND APPARATUS FOR DELIVERING ELECTROTHERAPY HAVING AN EQUIVALENT PROBABILITY OF SUCCESS FOR DIFFERENT PATIENTS

(75) Inventors: Joseph L. Sullivan, Kirkland, WA (US); Gary DeBardi, Kirkland, WA (US)

(73) Assignee: Medtronic Physio-Control Manufacturing Corporation., Redmond, WA (US)

( * ) Notice: Subject to any disclaimer, the term of this patent is extended or adjusted under 35 U.S.C. 154(b) by 306 days.

(21) Appl. No.: 09/841,183

(22) Filed: Apr. 23, 2001

(65) Prior Publication Data

US 2002/0183790 A1 Dec. 5, 2002

(51) Int. Cl.[7] ................................................. A61N 1/39
(52) U.S. Cl. ................................... 607/6; 607/8; 607/7
(58) Field of Search ............................... 607/5–8, 27–28

(56) References Cited

U.S. PATENT DOCUMENTS

| | | |
|---|---|---|
| 3,782,389 A | 1/1974 | Bell |
| 3,842,841 A | 10/1974 | Brighton et al. |
| 4,363,324 A | 12/1982 | Kusserow |
| 4,630,615 A | 12/1986 | Yomtov |
| 4,917,093 A | 4/1990 | Dufresne et al. |
| 5,036,850 A | 8/1991 | Owens |
| 5,069,211 A | 12/1991 | Bartelt et al. |
| 5,423,866 A | 6/1995 | Ekwall |
| 5,447,518 A | 9/1995 | Pless |
| 5,540,724 A | 7/1996 | Cox |
| 5,749,904 A | 5/1998 | Gliner et al. |
| 5,776,166 A | 7/1998 | Gliner et al. |
| 5,800,462 A | 9/1998 | Lopin et al. |
| 5,827,326 A | 10/1998 | Kroll et al. |
| 5,836,983 A | 11/1998 | Weijand et al. |
| 5,891,173 A | 4/1999 | Brewer |
| 5,908,442 A | 6/1999 | Brewer et al. |
| 5,944,742 A * | 8/1999 | Brewer et al. ................. 607/6 |
| 5,999,852 A | 12/1999 | Elabbady et al. |

FOREIGN PATENT DOCUMENTS

| | | |
|---|---|---|
| EP | 0 457 604 A2 | 11/1991 |
| EP | 0 457 604 A3 | 11/1991 |
| WO | WO 98/44990 | 10/1998 |

OTHER PUBLICATIONS

Dalzell, G.W.N., et al., "Initial Experience With a Microprocessor Controlled Current Based Defibrillator," *Br. Heart J. 61*:502–5, 1989.

Kerber, Richard E., et al., "Current–Based Transthoracic Defibrillation," *Am. J. Cardiol. 78*:1113–1118, 1996.

Kroll, Mark W., "A Minimal Model of the Single Capacitor Biphasic Defibrillation Waveform," *PACE 17*(Pt. I):1782–1792, 1994.

Lerman, Bruce B., et al., "Current–Based Versus Energy––Based Ventricular Defibrillation: A Prospective Study," *J. Am. Coll. Cardiol. 12*(5):1259–64, 1988.

Walcott, Gregory P., et al., "Choosing the Optimal Monophasic and Biphasic Waveforms for Ventricular Defibrillation," *J. Cardiovasc. Electrophysiol. 6*(9):737–750, 1995.

* cited by examiner

Primary Examiner—Jeffrey R. Jastrzab
(74) Attorney, Agent, or Firm—Ingrassia Fisher & Lorenz (57) ABSTRACT

A medical device constructed according to the invention includes electrodes (12a, 12b), a measuring unit (24) for measuring a patient-dependent electrical parameter (e.g., impedance) of the patient, an electrotherapy generator (26) for delivering electrotherapy to the patient, and a processing unit (20) for controlling the delivery of electrotherapy to the patient. Electrotherapy is preferably delivered to the patient based on the measured patient-dependent electrical parameter and a predetermined response of a reference patient to a nominal electrotherapy. The actual electrotherapy delivered to the patient is controlled so that the electrotherapy has a probability of success for the patient that is equivalent to the probability of success of the nominal electrotherapy for the reference patient. A consistent shock efficacy across different patients is achieved.

38 Claims, 4 Drawing Sheets

METHOD AND APPARATUS FOR DELIVERING ELECTROTHERAPY HAVING AN EQUIVALENT PROBABILITY OF SUCCESS FOR DIFFERENT PATIENTS

FIELD OF THE INVENTION

The invention relates generally to electrotherapy and, more particularly, to delivery of electrotherapy to patients having different physiological characteristics.

BACKGROUND OF THE INVENTION

One significant challenge to manufacturers of medical equipment that provide electrotherapy to patients is patient variability. Different patients have different physiological characteristics, such as transthoracic impedance, that may affect the efficacy of treatment provided to them. A device that provides electrotherapy to one patient with success may not be successful when providing the same treatment to a different patient because of differences in the patient's physiological make-up.

Ventricular fibrillation is one life-threatening medical condition that is treated by application of electrotherapy. Electrotherapy in the form of a defibrillation pulse must be strong enough to stop the heart's unsynchronized electrical activity and give the heart a chance to reinitiate a synchronized rhythm. Resistance to the flow of electrical current through a patient's thorax is known as transthoracic impedance, and is typically measured in ohms.

An external defibrillator may be used with different patients having a wide range of transthoracic impedance. Conventional defibrillators are often specified for and tested with 50 ohm loads (to represent a "standard" or "reference" patient). However, the actual transthoracic impedance of patients can vary greatly in a range from 20 to 300 ohms, though most patients typically fall in a range of 25 to 180 ohms.

Defibrillation pulses that are effective (i.e., successful) in treating low impedance patients may not necessarily deliver effective treatment to high impedance patients, and vice versa. For instance, too little current in a defibrillation pulse may not be effective in defibrillating the patient's heart. On the other hand, too much current in a defibrillation pulse can be inefficient, and more importantly, may damage a patient's tissue. The risk of damage to a patient's myocardium from a large defibrillation shock suggests that defibrillation should be attempted with the lowest current practicable, consistent with a desired probability of success for the defibrillation therapy.

Different approaches exist in the prior art for delivering defibrillation therapy to patients having different transthoracic impedance. One approach seeks to deliver a constant amount of current to each patient, regardless of the patient's impedance. The defibrillation pulse generated by the defibrillator is adjusted in response to a measurement of the patient's impedance so that the current delivered by the defibrillator to each patient remains constant. In practice, however, it is difficult to achieve delivery of a constant amount of current in an external defibrillator. See, e.g., U.S. Pat. No. 5,908,442 to Brewer, which describes delivery of a stepped truncated defibrillation waveform.

Another approach to delivering defibrillation therapy is to measure the patient's impedance and adjust the defibrillation pulse to maximize the patient's cardiac response to the defibrillation pulse. For instance, U.S. Pat. No. 5,908,442 further describes computation of a waveform duration that is intended to maximize the response of the patient's cardiac cell membranes to the defibrillation pulse. The computation is derived from a defibrillator circuit and patient model, which includes a representation of the patient's transthoracic impedance. However, when attempting to maximize the response of a patient's cardiac cell, more voltage may be applied to the patient than is needed to successfully defibrillate the patient, potentially damaging the patient.

Moreover, delivering a defibrillation pulse intended to maximize a patient's cardiac cell response results in different patients receiving different levels of defibrillation therapy that may or may not be effective in treating the patient. The present invention provides a solution for these problems and other shortcomings in the prior art.

SUMMARY OF THE INVENTION

The present invention provides a medical device and method for delivering electrotherapy to different patients that results in an equivalent probability of success in the different patients. A medical device constructed according to one exemplary embodiment of the invention includes electrodes adapted to be placed on a present patient, a measuring unit in communication with the electrodes for measuring a patient-dependent electrical parameter, such as impedance, of the patient, and an electrotherapy generator in communication with the electrodes for delivering electrotherapy to the patient. The medical device further includes a processing unit for controlling the electrotherapy delivery to the patient. The processing unit is configured to cause the electrotherapy generator to deliver electrotherapy that is adjusted for the patient based on the patient's measured patient-dependent electrical parameter. In one implementation, a predetermined response of a reference patient to a nominal electrotherapy is used. The actual electrotherapy delivered to the present patient is controlled so that the electrotherapy has a probability of success for the present patient that is equivalent to the probability of success of the nominal electrotherapy for the reference patient. One implementation of the invention produces a model response in the present patient that is equivalent to the predetermined response of a reference patient model to the nominal electrotherapy.

In accordance with one aspect of the invention, a nominal electrotherapy is selected for delivery to a present patient. During a preprocessing stage, the response of a reference patient to the nominal electrotherapy is determined. The reference patient is characterized to have a patient-dependent electrical parameter (such as impedance) of a reference amount. A corresponding patient-dependent electrical parameter is measured in the present patient. The delivery of electrotherapy to the present patient is then controlled based on the patient's measured patient-dependent electrical parameter and the determined response of the reference patient to the nominal electrotherapy. The actual electrotherapy delivered to the present patient has a probability of success that is equivalent to the probability of success of the nominal electrotherapy for the reference patient.

The delivery of electrotherapy to a present patient may be controlled in accordance with a translation factor determined during a preprocessing stage. The preprocessing stage in one embodiment of the invention includes determining the model response of a reference patient to a nominal electrotherapy. Also determined are the model responses of different patients to the nominal electrotherapy. The preprocessing includes comparing the model response of the reference patient with the model response of the different patients to the nominal electrotherapy, and determining an adjustment that compensates for relative differences between the model response of the reference patient and the model response of the different patients. The determined adjustment is used to modify the nominal electrotherapy to produce an actual electrotherapy for a present patient. The actual electrotherapy produces a model response in the patient that is equivalent to the model response of the reference patient to the nominal electrotherapy, with an equivalent probability of success. The patient-dependent electrical parameter used in characterizing the different patients may be an impedance of the patients, such as transthoracic impedance.

In another embodiment of the invention, the preprocessing stage includes evaluating the response of a number of different patients to electrotherapy. By empirical analysis, levels of electrotherapy are determined for different patients that result in a probability of success that is equivalent for all of the patients. While there may not be an explicit predetermined response of a reference patient model that is used to guide the determination of actual electrotherapy (to achieve an equivalent success rate in all patients), a predetermined model response is implicitly used, namely, the response to be produced in all of the patients that yields the desired probability of success. A patient-dependent electrical parameter, such as transthoracic impedance, that distinguishes the different patients, is used in preparing the translation factor that translates a nominal electrotherapy to an actual electrotherapy for a present patient.

One of the benefits of the present invention is that it avoids attempting to deliver inappropriately low energy levels to a patient with high impedance, and likewise, avoids delivering high-energy shocks to patients with low impedance which could result in excessive current flow, myocardial damage, and failure to defibrillate. Instead, a defibrillator constructed according to the present invention delivers defibrillation therapy tailored for the patient to have an equivalent probability of success for the patient as for other patients.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Electrotherapy in the form of one or more electric pulses applied to a patient can produce a therapeutic response in the patient. For example, delivering one or more defibrillation pulses to a patient can be effective in treating ventricular fibrillation, depending on the amplitude and duration of the defibrillation pulse. In other circumstances, electrotherapy in the form of lower-magnitude pacing pulses may help a patient sustain a regular cardiac rhythm. Other forms of electrotherapy may also be delivered to a patient depending on medical indications in the patient.

The present invention is directed to apparatus and methods for delivering electrotherapy to different patients that has an equivalent probability of success in the different patients. An electrotherapy is successful when it produces in a patient a desired physiological response. For example, a successful defibrillation pulse is one that defibrillates a patient's heart, with the heart returning to a synchronized rhythm. A pacing pulse is successful when it triggers a contraction of the heart. The probability of success, or success rate, of an electrotherapy represents the likelihood that the electrotherapy will produce a successful result for a particular patient. Determining the amount of electrotherapy to be delivered to a patient, which is a primary factor that influences the probability of success of the electrotherapy, includes balancing the probability of success with the possibility of damage to the patient (which may occur if the amount of electrotherapy is set too high).

One exemplary embodiment of the invention provides defibrillation therapy that produces an equivalent voltage across the heart cells of a higher impedance patient (e.g., a 100 ohm patient) as a reference impedance patient (e.g., a 50 ohm patient). In one embodiment of the invention, producing an electrotherapy that has an equivalent probability of success in different patients is accomplished by first determining a model response of a reference patient (e.g., 50 ohm patient) to a nominal electrotherapy, and then assessing the relative change in response when the electrotherapy is delivered to a different patient (e.g., 100 ohm patient). While actual heart cell voltage of patients may not be known or determined, it is possible, in accordance with the invention, to determine the relative change in model cell response from a reference patient to another patient. In the defibrillator embodiment of the invention referenced above, the magnitude and/or duration of the actual defibrillation pulse delivered to a patient is adjusted so as to produce a model cell voltage in the patient that is equivalent to the model cell voltage that results in the reference patient from delivery of the nominal electrotherapy. Embodiments of the invention that provide other forms of electrotherapy, such as pacing, may similarly adjust the electrotherapy according to a relative change in model response from a reference patient to another patient, to produce an equivalent model response, and hence equivalent probability of success in all patients.

Figure 1:
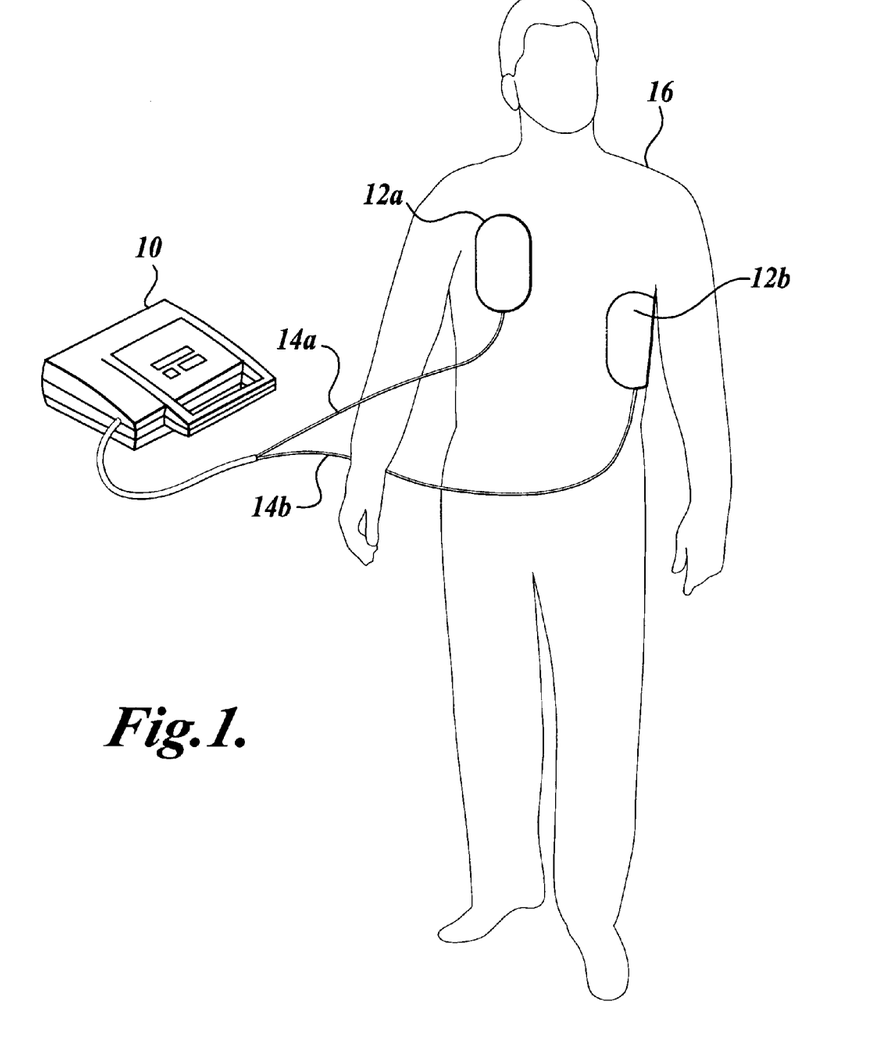
FIG. 1 is a pictorial diagram of a defibrillator constructed in accordance with the present invention and attached to a patient.

FIG. 1 illustrates a defibrillator 10 constructed in accordance with the present invention. The defibrillator 10 is an exemplary embodiment of the invention discussed extensively herein only to illustrate the principles of the invention. The present invention is contemplated for use in a wide variety of medical devices that provide electrotherapy.

Referring to FIG. 1, electrodes 12a and 12b, when placed on a patient 16, connect the defibrillator 10 to the patient 16. The electrodes 12a and 12b are connected to the defibrillator 10 via wires 14a and 14b. The defibrillator 10 produces a defibrillation pulse by first accumulating a high-energy electric charge in an internal energy store, typically a capacitor. Upon activation of a switching mechanism in the defibrillator 10, the defibrillator delivers the stored energy to the patient 16 via the electrodes 12a and 12b. The resultant discharge of the defibrillator capacitor causes a large electric pulse to be transferred through the patient.

The electrodes 12a and 12b shown in FIG. 1 may be hand-held electrode paddles or adhesive electrode pads placed on the skin of the patient 16. When the electrodes 12a and 12b are applied to the patient 16, the patient's body provides an electrical path between the electrodes. If hand-held electrode paddles are used, the defibrillator 10 preferably prompts the operator of the defibrillator to maintain the paddles firmly on the patient's body throughout the defibrillation procedure of the present invention.

Figure 2:
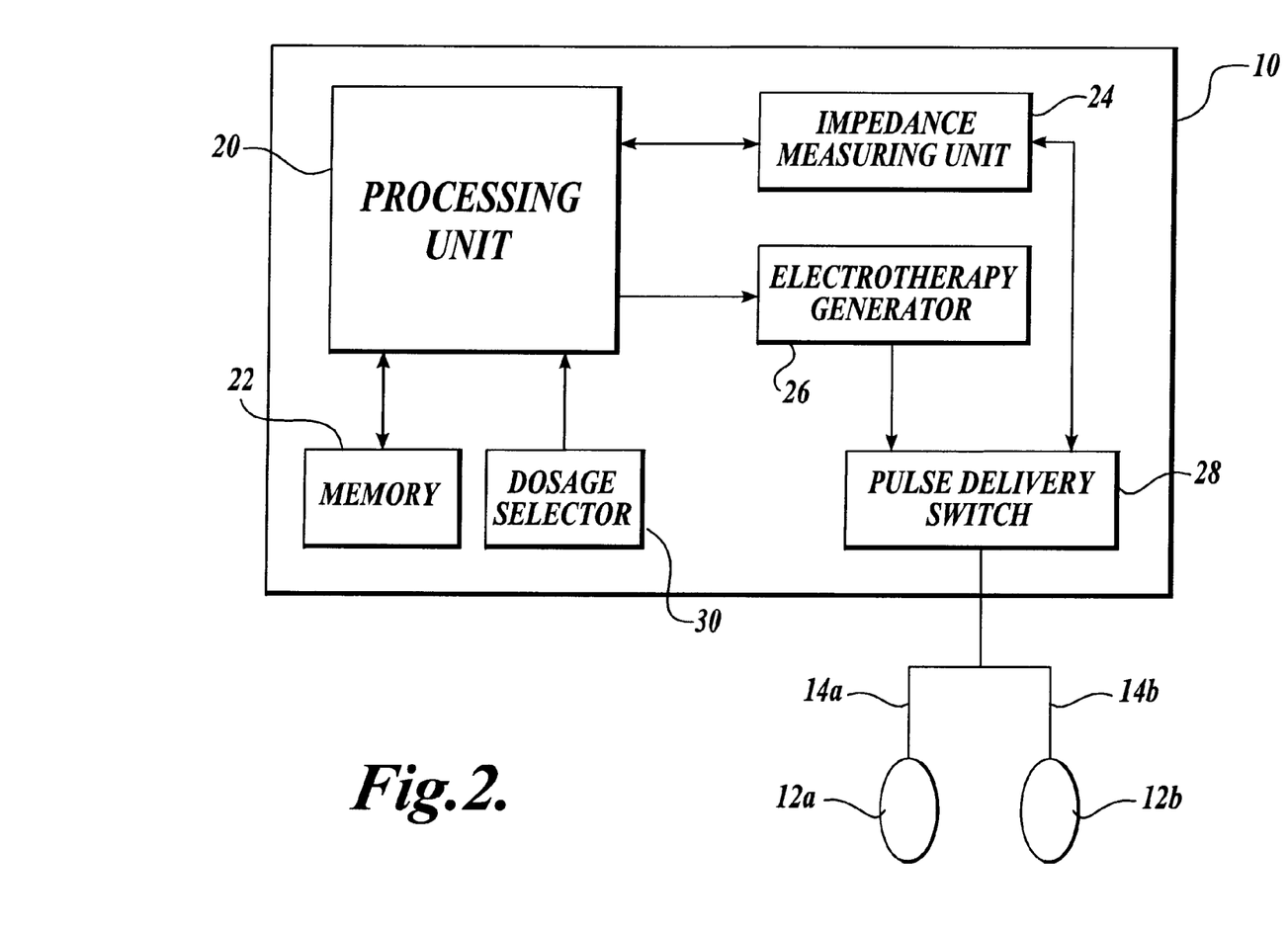
FIG. 2 is a diagram illustrating major functional blocks of the defibrillator shown in FIG. 1.

Prior to discussing the operation of the defibrillator 10, it is useful to note certain major functional blocks internal to the defibrillator 10, as illustrated in FIG. 2. It should be understood that two or more of the functional blocks shown in FIG. 2 may be integrated, as desired, when actually implementing the present invention. For example, the impedance measuring unit 24, as discussed below, may be fully or partially integrated with the processing unit 20, or the function of the impedance measuring unit 24 may be implemented by the processing unit 20.

In FIG. 2, the defibrillator 10 includes a processing unit 20 that controls the operation of the defibrillator in accordance with program instructions stored in memory 22. The processing unit 20 may, for example, be a standard microprocessor that is well-known in the art. Similarly, the memory 22 may be comprised of a standard form of computer memory, such as a form of ROM, RAM, or disk. Preferably, the memory 22 is rewriteable so that software updates may be entered into the memory to upgrade the operation of the defibrillator 10. The memory 22 may also be used to store data collected by the defibrillator 10 for display and/or later download to a separate computing device.

The processing unit 20 governs the operation of an impedance measuring unit 24 and an electrotherapy generator 26. In accordance with one aspect of the invention, discussed in more detail below, the defibrillator 10 measures a patient-dependent electrical parameter (such as transthoracic impedance) of a patient before delivering a defibrillation pulse to the patient. In reference to FIGS. 1 and 2, the defibrillator 10 measures the patient's transthoracic impedance between the electrodes 12a and 12b using the impedance measuring unit 24. The impedance measuring unit 24 suitably employs any of several known impedance measuring techniques, including a high-frequency, low-level current pulse technique, a sensing resistance technique, or a low intensity sensing shock technique. The impedance measuring unit 24 may also measure transthoracic impedance during the delivery of a defibrillation pulse.

Preferably, a high-frequency, low-level current technique is used for measuring patient impedance (outside of delivering an actual defibrillation pulse). A pulse generator in the impedance measuring unit 24 produces low amplitude, constant current, pulses. The pulses are generated at a frequency in a range generally from 5–100 kHz. In one actual embodiment, the pulses are configured at around 62 kHz. The pulses flow from one patient electrode 12a through the patient's body to the other patient electrode 12b. The voltage that develops across the patient's body as a result of the pulses is proportional to the product of the patient's transthoracic impedance and the applied current. The impedance measuring unit 24 measures the voltage across the patient and calculates the patient's impedance by dividing the voltage measurement by the applied current. Of course, other methods and means of measuring a patient-dependent electrical parameter may suitably be used in the invention.

A pulse delivery switch 28 in the defibrillator 10 connects the impedance measuring unit 24 to the patient electrodes 12a and 12b for measurement of the patient's impedance. The pulse delivery switch 28 and/or impedance measuring unit 24 may include conventional analog-to-digital converting circuitry that converts the current and/or voltage information sensed at the electrodes 12a and 12b to digital form for processing. In other embodiments, the impedance measuring unit 24 may be directly connected to the patient electrodes 12a and 12b, by passing the switch 28. Preferably, the impedance measuring unit 28 will have appropriate protection from the high voltages of a defibrillation pulse being delivered to the patient.

The patient's transthoracic impedance may also be measured using a patient-dependent electrical parameter sensed by the defibrillator 10 during prior defibrillation pulses, if any, delivered to the patient. Such parameter measurement may include an analysis of the voltage and current that developed in the patient during the prior defibrillation pulse. Alternatively, it may include an analysis of the drop in voltage in the defibrillator capacitor (included in the electrotherapy generator 26) over a period of time during the discharge. Given a known capacitance and resistance internal to the defibrillator 10, the patient's impedance can be determined based on the contribution of the patient's impedance to the capacitor voltage rate of decay. Measuring the patient's impedance during a prior defibrillation pulse, if any, may help ensure that an accurate impedance measurement is used for controlling subsequent defibrillation pulses in accordance with the present invention. In some circumstances, it may be advantageous to combine impedance measurements made during prior defibrillation pulses with a predefibrillation impedance measurement made using a high-frequency, low-level current pulse technique.

After measuring a patient-dependent electrical parameter in the patient, the processing unit 20 uses the measured patient parameter data to control the electrotherapy to be delivered to the patient. For example, in the embodiment of the invention depicted in FIG. 2, the processing unit 20 receives the patient impedance measurement from the impedance measuring unit 24 and controls the delivery of the defibrillation therapy from the electrotherapy generator 26.

The defibrillation therapy delivered by the defibrillator 10 may be a multiphasic pulse. One such multiphasic defibrillation pulse is a biphasic truncated exponential pulse. At appropriate time(s) determined by the processing unit 20 or electrotherapy generator 26, the pulse delivery switch 28 connects the electrotherapy generator 26 to the patient via the electrodes 12a and 12b and wires 14a and 14b, causing the defibrillation pulse to discharge through the patient. Preferably, the pulse delivery switch 28 controls the polarity of the pulse being delivered to the patient. A suitable H-bridge switch for delivery of a biphasic defibrillation pulse is described in U.S. Pat. No. 6,175,765, titled "H-Bridge Circuit for Generating a High-Energy Biphasic Waveform in an External Defibrillator," which is commonly assigned to the assignee of the present application and is incorporated by reference herein. Other suitable switching, including mechanical relays, may be used in the pulse delivery switch 28, if desired.

Finally, the defibrillator 10, as shown in FIG. 2, further includes a dosage selector 30 that is used by the operator of the defibrillator 10 to indicate the electrotherapy to be provided to the patient. The electrotherapy dosage may be specified in terms of voltage, amperes, energy, or other suitable units of measure. The dosage selector 30 may be in the form of a continuous dial or meter. Alternatively, the dosage selector 30 may provide dosage selection from a set number of discrete choices (e.g., 100 joules, 200 joules, 300 joules, and 360 joules, if dosage selection is provided in terms of energy). In other embodiments of the defibrillator 10 (e.g., an automated external defibrillator with a preprogrammed therapy protocol), the dosage selector may be eliminated with the dosage selection and patient-specific adjustments being made automatically by the defibrillator.

It is worthwhile to note that dosage selection presents a special consideration in terms of the present invention. As will be appreciated from the discussion of the invention herein, the actual amount of electrotherapy (e.g., joules of energy) delivered to a patient may be adjusted upward or downward from a nominal selection indicated by the operator via the dosage selector 30, depending on the magnitude of the patient-dependent electrical parameter (e.g., impedance) measured in the patient. In this regard, at least initially, the dosage selector 30 more appropriately provides the operator an opportunity to indicate the level, or degree, of electrotherapy to be provided to the patient, as opposed to mandating the actual amount of therapy (e.g., specific number of joules) to be delivered to the patient. In some embodiments of the invention, however, it may be desirable to permit the operator to override the adjustment provided by the present invention and mandate the actual amount of the therapy to be delivered.

In order to fully understand and appreciate the ongoing operation of the defibrillator 10 (or other medical device providing electrotherapy in accordance with the present invention), it is first necessary to understand the principles underlying the present invention. It is also necessary to understand the preprocessing that is performed to prepare the defibrillator 10 to control (i.e., adjust) the delivery of electrotherapy for different patients so that electrotherapy with an equivalent probability of success in the different patients is achieved.

Over a number of years, researchers have prepared various quantitative models that are intended to represent the electrical characteristics of electrotherapy device/patient systems. For a defibrillator/patient system, as shown in FIG. 1, a quantitative model would typically include, in simplified form, various resistive and capacitive (and possibly inductive) elements that represent the electrical characteristics of the defibrillator 10. The model would also include a representation of the patient 16 by including an additional arrangement of resistive and capacitive (and possibly inductive) components.

Figures 3, 5:
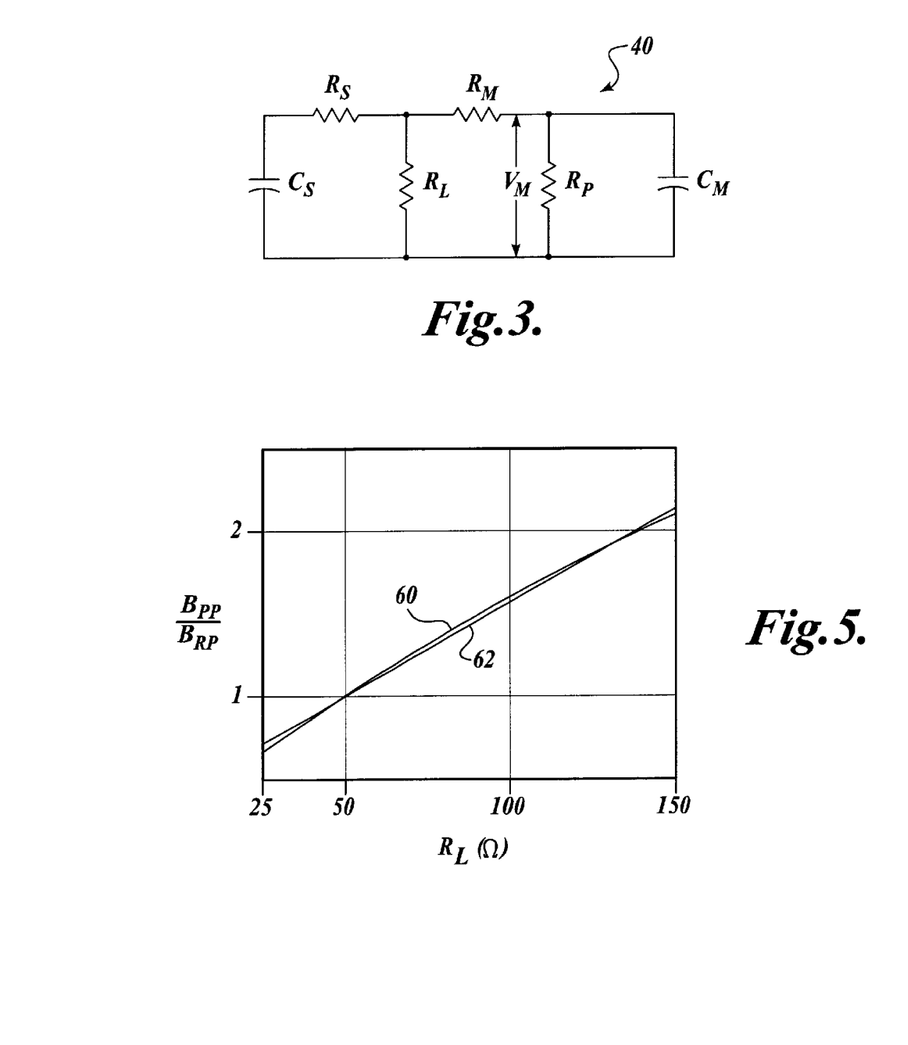
FIG. 3 is a circuit diagram providing an exemplary defibrillator/patient system model for use in evaluating a patient's model response to defibrillation therapy.
FIG. 5 is a graph showing a ratio derived from comparing the model response of different patients with the model response of a reference patient, and an accompanying best-fit line approximation of the ratio.

FIG. 3 illustrates one exemplary defibrillator/patient system model 40. In the model 40, the (simplified) electrical characteristics of the defibrillator 10 are represented by capacitor $C_s$, which represents the main storage capacitor for the electrical energy to be delivered to the patient, in series with resistance $R_s$, which represents the internal impedance of the device. The remaining components illustrated in FIG. 3 represent various aspects of the patient, including $R_L$, which represents the transthoracic impedance of the patient.

The resistor-capacitor (RC) circuit forming the right-hand portion of FIG. 3 represents the electrical characteristics of a cell in the patient's myocardium. The model cell has a membrane resistance $R_M$ in series with a parallel resistance $R_P$ and a membrane capacitance $C_M$. The voltage $V_M$ measured across resistance $R_P$ and capacitor $C_M$ represents the voltage that develops across the model cardiac cell membrane when electrical energy is delivered from the capacitor $C_S$. Further detail regarding the model cell aspect of the defibrillator/patient model 40 is provided in *A Minimal Model of the Single Capacitor Biphasic Defibrillation Waveform*, by Mark W. Kroll, PACE, Vol. 17, November 1994, pp. 1782–92, Appendix, incorporated by reference herein.

In one embodiment of the invention, a quantitative model of an electrotherapy device/patient system is used to assess a patient's response to electrotherapy delivered from the device. The present invention extends the concept of system modeling by analyzing successful electrotherapy delivered to a reference patient, and adjusting the electrotherapy for different patients to obtain an equivalent probability of success in the different patients. If electrotherapy is provided to other patients in a manner that produces a model response in the other patients that is equivalent to the model response of the reference patient, it follows that the electrotherapy should be equally successful in treating the other patients. In this manner, the present invention provides a system that achieves a consistent shock efficacy across different patients.

The probability of success of a defibrillation pulse is generally dependent on the voltage that develops across the patient's myocardium when the defibrillation pulse is discharged through the patient. When using a model of a defibrillator/patient system that includes a model myocardial cell, the probability of success of defibrillation may be related to the voltage that develops across the model cardiac cell. In the context of the model defibrillator/patient system 40 shown in FIG. 3, an equivalent model response in different patients is achieved when the voltage $V_M$ that develops across the model cardiac cell membranes of the different patients is equivalent to the voltage that develops across the model cell membrane in a reference patient. Electrotherapy such as defibrillation pulse can be achieved with an equivalent probability of success by generating an equivalent model response in all patients.

The model response of a reference patient is preferably determined during a preprocessing stage. The preprocessing stage involves assessing relative changes in model response when the electrotherapy is delivered to different patients. Based on the assessed relative changes in model response, the defibrillator 10 is configured to control the delivery of defibrillation therapy to patients so that the model cardiac response (i.e., $V_M$) of a present patient is equivalent to the previously-determined model cardiac response of a reference patient. Consequently, when referring to "the predetermined response of a reference patient to a nominal electrotherapy," it is not necessary that an actual myocardial cell voltage (or other patient parameter) be calculated for the reference patient (or, for that matter, the present patient). All that is needed is an expression (e.g., a mathematical function) that represents the patient's response. The determined expression for the reference patient can be compared to the determined expression for the present patient to yield the relative change in response, and the electrotherapy for the present patient can be adjusted, in accordance with the calculated relative change, to produce a model response in the present patient that is equivalent to the model response of the reference patient. For higher impedance patients (i.e., patients having a transthoracic impedance higher than the reference patient), the delivery of defibrillation therapy may be controlled, for example, by increasing the initial charge voltage on the capacitor $C_S$. For lower impedance patients, an equivalent model response may be accomplished by decreasing the initial charge voltage on capacitor $C_S$ (i.e., to a level less than that specified for the reference patient).

Figure 4:
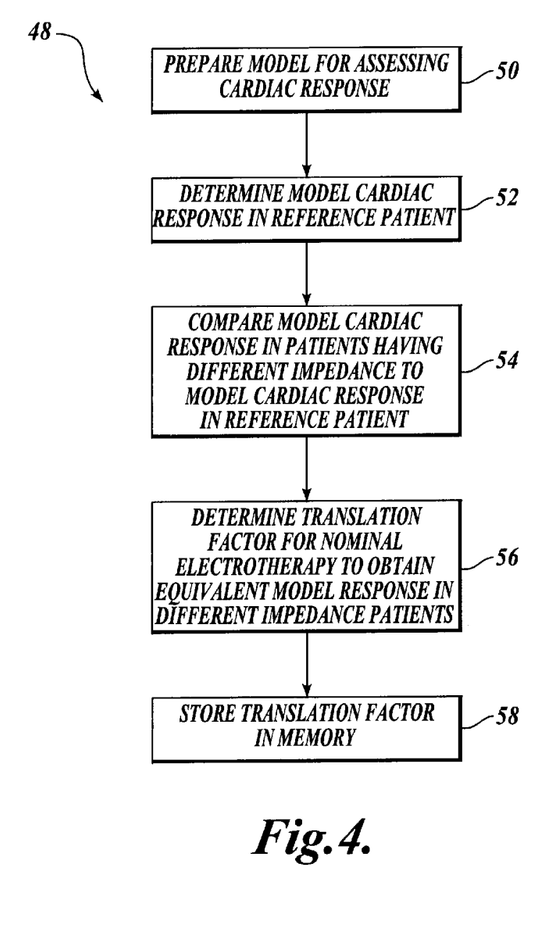
FIG. 4 is a flow diagram describing preprocessing performed in an impedance-based embodiment of the invention.

The flow diagram 48 in FIG. 4 describes preprocessing performed in one exemplary impedance-based embodiment of the present invention. Beginning at a block 50 in FIG. 4, the preprocessing 48 includes preparing a device/patient system model for assessing a patient's model response to a given electrotherapy. For example, a suitable model may be prepared as shown in FIG. 3 to assess the voltage $V_M$ that develops across a model myocardial cell of a patient during a defibrillation pulse.

At a block 52 in FIG. 4, the model cardiac response of a reference patient is determined using the system model prepared in block 50. If using the system model 40 shown in FIG. 3, an expression for the voltage response $V_M$ of the model heart cell may be derived for the reference patient. The voltage response $V_M$ suitably represents a model cardiac response of the patient.

Deriving of an expression for the model cardiac response $V_M$ requires an analysis of the system model 40. In one aspect, the system model 40 produces a defibrillator system time constant $\tau_s$ that is a product of the defibrillator capacitance $C_S$ and the combined defibrillator and patient impedance $R_S$ and $R_L$. The time constant $\tau_s$ is reflected in the rate of decay of voltage across the capacitor $C_S$ when the capacitor is discharging energy through the patient.

For the system model 40, an additional time constant $\tau_m$ may be assumed to represent the effect of the patient's myocardium on a defibrillation pulse. The time constant $\tau_m$ is a characteristic of the patient's heart. In one embodiment of the invention, $\tau_m$ is suitably set to equal 5.1 milliseconds. Additional detail relative to the time constant $\tau_m$ and other aspects of the derivation of $V_M$, as discussed herein, is provided in *Choosing the Optimal Monophasic and Biphasic Waveforms for Ventricular Defibrillation*, by Gregory P. Walcott, M.D., et al., *Journal of Cardiovascular Electrophysiology*, September 1995, pp. 737–50, incorporated by reference herein.

For purposes of determining a reference patient's model response in block 52, a reference patient impedance $R_L$ of 50 ohms may be assumed. Other embodiments of the invention may use a different impedance value, or other patient-dependent electrical parameter value, for the reference patient. We may further assume, for this example, the defibrillator 10 includes a defibrillator capacitor $C_S$ of 196 microfarads and an internal impedance $R_S$ of 5 ohms. The foregoing is summarized as follows:

$$C_S = 196 \times 10^{-6} F \quad (1)$$

$$R_S = 5 \text{ ohms} \quad (2)$$

$$\tau_s = C_S(R_L + R_S) \quad (3)$$

$$\tau_m = 0.0051 \text{ s} \quad (4)$$

In the above-referenced article by Walcott et al., a factor $\gamma$ is also defined as follows:

$$\gamma = \frac{\tau_s \tau_m}{\tau_s - \tau_m} \quad (5)$$

The initial peak current $I_o$ that is output from the defibrillator 10 may be defined as a function of the initial charge voltage $V_o$ (i.e., the voltage to which the capacitor $C_S$ is charged) divided by the combined impedance of the defibrillator/patient system:

$$I_o = \frac{V_o}{R_L + R_S} \quad (6)$$

Using Equations (1)–(6) above, the model cell membrane $V_M$ may be given (as a function of time for the time period in which the capacitor $C_S$ is discharging energy through the patient) as follows:

$$V_M = I_o \gamma e^{\frac{-t}{\tau_m}} \left( e^{\frac{t}{\gamma}} - 1 \right) \quad (7)$$

If the values in Equations (1)–(4) are assumed, the model response $V_M$ may be evaluated once the initial charge voltage $V_0$, the patient impedance $R_L$, and the time t are specified. The initial charge voltage $V_0$ is normally predetermined based on the amount of therapy to be delivered to the patient. Additional discussion regarding the selection of $V_o$ for different levels of defibrillation therapy is discussed below in reference to FIG. 6. The model response $V_M$ may be evaluated at any time "t" during the delivery of the defibrillation pulse. In the embodiment of the invention discussed herein, $V_M$ is evaluated at a time "$t_1$" that defines the end of the defibrillation pulse (for a monophasic pulse) or the end of the first phase (for a multiphasic pulse). The selection of a time $t_1$ for evaluating the model response of a patient may depend, in part, on the shape of waveform to be delivered.

Persons skilled in the art of defibrillation will appreciate that a variety of defibrillation pulse waveforms may be used in the present invention. One embodiment of the invention uses a truncated exponential defibrillation waveform. The defibrillation energy being discharged in a truncated exponential defibrillation waveform is truncated at a selected time "$t_1$" by disconnecting the capacitor $C_S$ from the patient. Researchers have proposed various techniques for determining an optimal time $t_1$ for truncating the pulse delivery. While for purposes of the present invention any suitable time to truncation may be used, one embodiment of the invention adopts methodology proposed in the above-referenced article by Walcott et al. The authors Walcott et al. use a quantitative model to predict optimal truncation points for monophasic and first phase of biphasic waveforms with the intent to minimize the leading edge voltage needed for successful defibrillation. In the Walcott et al. model, an optimal phase duration (i.e., truncation time $t_1$) is determined to be:

$$t_1 = -\gamma \ln\left(\frac{\tau_m}{\tau_s}\right) \quad (8)$$

In Equation (8), the variables $\tau_s$, $\tau_m$, and $\gamma$ are as defined above in Equations (3)–(5). Since $\tau_s$ represents the time constant of the defibrillator system as attached to a patient, $\tau_s$ is mathematically related to the patient's impedance. As a result, the time $t_1$ in Equation (8) relates a calculation of optimal phase duration to the patient's impedance.

The delivery of electrotherapy, according to the invention, is controlled based on an evaluation of relative differences in model response between a reference patient and other patients. For this evaluation, it is sufficient to use an equation describing the model response, as shown in Equation (7). Using an equation for the model response, a comparison of the model response of the reference patient and the other patients can be performed, as indicated in block 54, without requiring a determination of an actual value for the model patient response.

The model cardiac cell response $V_M$, as described in Equation (7), is dependent on the patient impedance $R_L$. Accordingly, when electrotherapy is delivered to a present patient having an impedance higher or lower than the impedance of a reference patient, the model cardiac response in the present patient will vary from the response in the reference patient, unless an adjustment to the electrotherapy is made. A predetermined translation factor is used in one embodiment of the invention to control the electrotherapy so that the electrotherapy, when delivered to a present patient, produces the same model response in the present patient as the model response of the reference patient (resulting in an equivalent probability of success for the electrotherapy delivered to the patients). The translation factor may be used, for example, to adjust the initial capacitor charge voltage $V_o$ from a level prescribed for the reference patient to a level for the present patient, based on a measurement of the present patient's impedance.

The translation factor is comprised of a value or equation preferably determined during the preprocessing stage, as indicated in block 56 in FIG. 4. The translation factor is determined based on the relative differences in model response between the reference patient and other patients to a nominal electrotherapy. One suitable approach to evaluate the relative differences in model response is to insert an additional variable into the equation describing the model response. The additional variable may be multiplied against one of the waveform parameters over which the electrotherapy device has control. For example, extending the equation for $V_M$ set forth in Equation (7), the following equation for $V_M$ includes a variable B that is multiplied against the initial charge voltage Vo:

$$V'_M = \left(\frac{BV_o}{R_L + R_s}\right) \gamma e^{\frac{-t}{\tau_m}} \left(e^{\frac{t}{\gamma}} - 1\right) \quad (9)$$

Comparing Equation (9) with Equation (7), one skilled in the art will recognize that as patient impedance $R_L$ varies from patient to patient, variable B may be adjusted so that the model cardiac response $V_M$ remains constant across all patients. Solving for variable B results in:

$$B = \frac{V'_M}{V_o} \cdot \frac{R_L + R_S}{\gamma} \cdot \frac{e^{\frac{t}{\tau_m}}}{e^{\frac{t}{\gamma}} - 1} \quad (10)$$

To determine an appropriate translation factor, as indicated at block 56 in FIG. 4, the variable B for various patients (whose impedance $R_L$ varies over a range of values) is compared with the variable B for the reference impedance patient (whose impedance $R_L$ is set at a reference amount). In the comparison, the initial factor $V_M/V_o$ can be dropped since that factor is a constant. For a present patient, Equation (10) may thus be rewritten as:

$$B_{PP} = \frac{R_L + R_S}{\gamma} \cdot \frac{e^{\frac{t}{\tau_m}}}{e^{\frac{t}{\gamma}} - 1} \quad (11)$$

and for a reference patient (having a reference impedance of 50 ohms), Equation (10) may be rewritten as:

$$B_{RP} = \frac{50 + R_S}{\gamma} \cdot \frac{e^{\frac{t}{\tau_m}}}{e^{\frac{t}{\gamma}} - 1} \quad (12)$$

Turning to FIG. 5, the curve 60 depicts a ratio of the variable B for the present patient (labeled $B_{PP}$) to the variable B for the reference patient (labeled $B_{RP}$). For $B_{PP}$ in FIG. 5, Equation (11) is used wherein $R_L$ is varied from 25 to 150 ohms. A calculation of time $t_1$ from Equation (8) is substituted in Equation (11) for the variable t. The remaining variables in Equation (11) are as set forth in Equations (1)–(5).

For $B_{RP}$ in FIG. 5, the patient impedance $R_L$ is set at a reference amount (e.g., 50 ohms, in this case), with time $t_1$, as calculated in Equation (8), substituted for the variable t. As would be expected, time $t_1$ for $B_{RP}$ is calculated using $R_L$ of 50 ohms (i.e., the reference impedance).

The ratio of $B_{PP}$ to $B_{RP}$ illustrates the amount by which the electrotherapy provided to the reference patient must be adjusted in order to produce an equivalent model response in the present patient. If the impedance of the present patient equals the impedance of the reference patient, then $B_{PP}$ equals $B_{RP}$, and the adjustment amount is 1 (meaning no voltage adjustment is necessary), as shown in FIG. 5.

For simplicity, the curve 60 shown in FIG. 5 may be approximated by a best-fit linear equation. One such linear approximation produces the line 62. If circumstances are such that a linear approximation of the $B_{PP}/B_{RP}$ ratio is not satisfactory, another form of curve approximation may be used. Regardless, the resulting approximation equation constitutes a translation factor "TF" that is used in adjusting the electrotherapy to be provided to different patients. For the example given in FIG. 5, the line 62 (i.e., translation factor TF) may be described as:

$$TF = 0.01088 R_L + 0.456 \quad (13)$$

Note that FIG. 5 assumes a reference impedance of 50 ohms. In an alternative embodiment of the invention that uses a reference patient impedance of 80 ohms, for example, the translation factor TF may be 0.008174 $R_L$+0.34608.

Returning to the preprocessing described in FIG. 4, once a suitable translation factor TF is determined, such as Equation (13), the translation factor is preferably stored in memory, as indicated at block 58. The preprocessing in FIG. 4 may be repeated for a number of different levels of nominal electrotherapy (e.g., 200 joules, 300 joules, 360 joules, etc. for a defibrillation pulse), each time with the resulting translation factor for a level of therapy being stored in memory in association with the level of therapy to which it pertains. A look-up table in the memory can be used to organize the stored translation factor(s).

Figure 6:
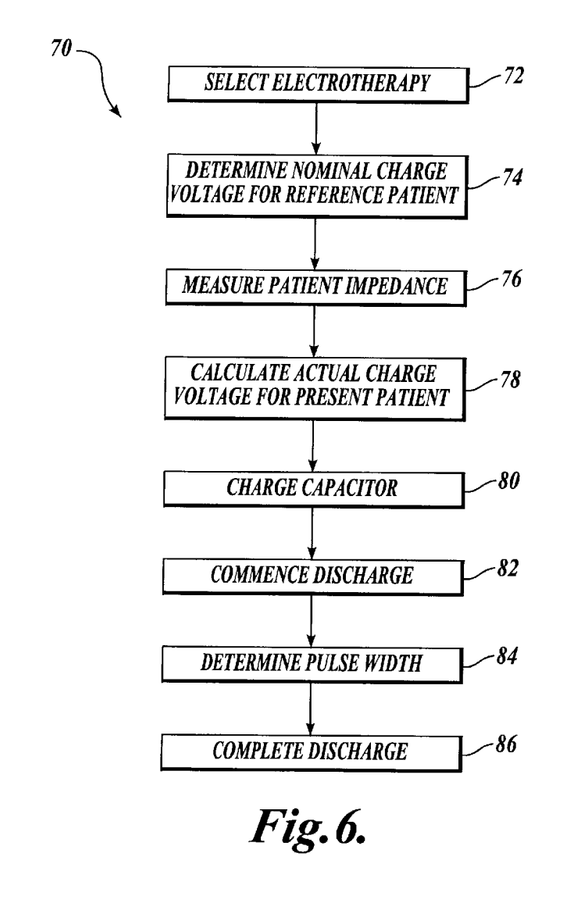
FIG. 6 is a flow diagram illustrating a method according to the present invention for controlling the delivery of a defibrillation pulse to produce an equivalent model response in different patients.

The ongoing operation of an electrotherapy device constructed according to one embodiment of the invention uses the translation factor to adjust the electrotherapy to be provided to a patient. FIG. 6 is a flow diagram of a procedure 70 illustrating the ongoing operation of one such embodiment of the invention, as implemented in a defibrillator. In the procedure 70, beginning at block 72, the operator of the defibrillator selects the electrotherapy to be provided to the patient. If the device is a defibrillator that specifies its dosage in terms of energy, for example, the operator selects a nominal amount of energy representing the level of therapy to be provided to the patient. Dosage selection is understood by the operator in terms relative to a reference patient. Thus, if the operator of the defibrillator selects a dosage of 200 joules, for example, the operator has a general sense for the level of electrotherapy to be provided to the patient. In the present invention, the actual number of joules delivered to the patient may vary from the nominal number of joules specified by the dosage selection depending on a patient-dependent electrical parameter such as impedance measured in the patient. The actual energy delivered may be adjusted upward or downward based on the measured patient-dependent parameter to ensure that the electrotherapy produces a model response in the patient that is equivalent to the model response that the reference patient would have had to the selected nominal dosage.

At block 74 in FIG. 6, the defibrillator 10 determines a nominal charge voltage for the defibrillator capacitor. The nominal charge voltage is set relative to the reference impedance patient and the selected nominal electrotherapy. The nominal charge voltage is the initial charge voltage $V_o$ to which the defibrillator capacitor is charged if the impedance of the present patient is the same as the reference patient.

Preferably, nominal charge voltage values are predetermined for various levels of electrotherapy and stored in memory. In a defibrillator system where the dosage is specified in terms of energy, a nominal charge voltage may be determined using a reverse calculation of the amount of energy conveyed by a defibrillation pulse to a patient. The purpose of this reverse calculation is to set the nominal charge voltage to a level that causes the defibrillation pulse, when discharged through the reference patient, to convey the specified amount of energy to the reference patient. A measure of energy delivered by a truncated exponential waveform to a patient may be given as follows:

$$E_d = \frac{V_o^2}{2} C_s \left(\frac{R_L}{R_L + R_S}\right)[1 - (1 - T_o)^2] \quad (14)$$

where $E_d$ is the energy delivered, $V_o$ is the nominal charge voltage, and $T_o$ is a tilt characteristic of the defibrillation pulse. Values for $C_S$ and $R_S$ may be set as shown in Equations (1) and (2).

Tilt is a measure of the pulse amplitude decay during pulse delivery. More specifically, tilt is the ratio of the drop in pulse amplitude to the initial pulse amplitude over a period of time, and may be expressed as follows:

$$T_o = 1 - e^{\left[\frac{-d_o}{\tau_s}\right]} \quad (15)$$

In Equation (15), $\tau_s$ is as defined in Equation (3) and do is the duration of the pulse for the reference patient. For a defibrillator system that delivers a biphasic truncated exponential waveform having a second phase duration set at two-thirds the duration of the first phase, $d_o$ equals 1.667 times the first phase duration (e.g., $t_1$ calculated by Equation (8)).

Using Equations (14) and (15), and the assumptions set forth in Equations (1)–(3), a nominal initial charge voltage $V_o$ may be calculated for a given amount of energy to be delivered to the reference patient. For instance, in a therapy protocol where defibrillation pulses of 100 joules, 200 joules, 300 joules or 360 joules are commonly given to patients, nominal charge voltage values $V_o$ may be calculated for a reference impedance $R_L$ of 50 ohms for each of the specified energy levels. A suitable algorithm for determining an appropriate charge voltage for delivering a specified number of joules, as discussed above, is provided in commonly-assigned U.S. Pat. No. 5,999,852, titled "Defibrillator Method and Apparatus," incorporated by reference herein.

At block 76 in FIG. 6, the defibrillator 10 measures the present patient's transthoracic impedance. As discussed earlier, a high-frequency low-level current technique may be used for measuring the patient's impedance. The measured impedance is used to calculate an actual charge voltage $V_o$ for the present patient, as indicated in block 78. In that regard, a previously determined translation factor TF (e.g., as set forth in Equation (13)) may be used to calculate the actual charge voltage. In Equation (13), the patient's impedance, as measured in block 76, is substituted for the variable $R_L$. The resulting adjustment value, or translation value, is then multiplied against the nominal charge voltage determined in block 74 to yield the actual charge voltage for the present patient. The defibrillator 10 may commence charging the defibrillator capacitor to the nominal charge voltage before calculating the actual charge voltage.

At block 80, the defibrillator 10 charges the defibrillator capacitor to the actual charge voltage in preparation to deliver the defibrillation pulse to the patient. At the same time, the defibrillator 10 may report to the operator a calculation of an estimated amount of energy that is expected to be delivered to the patient. It may also report the actual charge voltage to the operator of the defibrillator. If desired, the defibrillator 10 may allow the operator of the defibrillator to override the voltage adjustment made by the present invention and allow the operator to instead mandate the actual amount of therapy to be provided to the patient. Depending on hardware limitations of the electrotherapy device and patient safety considerations, upper and lower limits may be imposed on the actual charge voltage to which the device is charged (e.g., for patients exceeding 175 ohms, the charge voltage for a 175 ohm patient may be used, and for patients lower than 25 ohms, the charge voltage for a 25 ohm patient may be used).

Once the defibrillator capacitor is appropriately charged to the desired charge voltage, the defibrillator 10 may commence the delivery of the defibrillation pulse, as indicated at block 82. Preferably, prior to the delivery, the operator of the defibrillator is advised that the pulse is ready for delivery. The defibrillator then awaits a signal from the operator to commence the delivery of the defibrillation pulse.

The present invention generally produces an output current that appears flatter across a range of different impedance patients than found in prior art fixed energy approaches. In one embodiment of the invention, the initial output current, relative to the initial current delivered to a reference patient of 80 ohms, is approximately 45% higher for a 40 ohm patient, 15% higher for a 60 ohm patient, 7% lower for a 100 ohm patient, and 16% lower for a 120 ohm patient.

In the procedure 70 illustrated in FIG. 6, it is noted that the duration of the defibrillation pulse is not determined prior to commencing the discharge of a defibrillation pulse. Patient-dependent parameters measured during the discharge of the defibrillation pulse have been found to provide useful information in selecting an effective pulse duration. One suitable algorithm for determining the pulse duration during the delivery of the defibrillation pulse, as indicated in block 84, is set forth in U.S. Provisional Patent Application No. 60/213,082, titled "Method and Apparatus That Uses A Time Measurement To An Electrical Parameter Threshold To Determine A Defibrillation Pulse Duration," filed Jun. 19, 2000 by the assignee of the present invention, and incorporated by reference herein. Given a pulse width determined in block 84, the delivery of the defibrillation pulse continues until the discharge is completed, as indicated in block 86.

Figure 7:
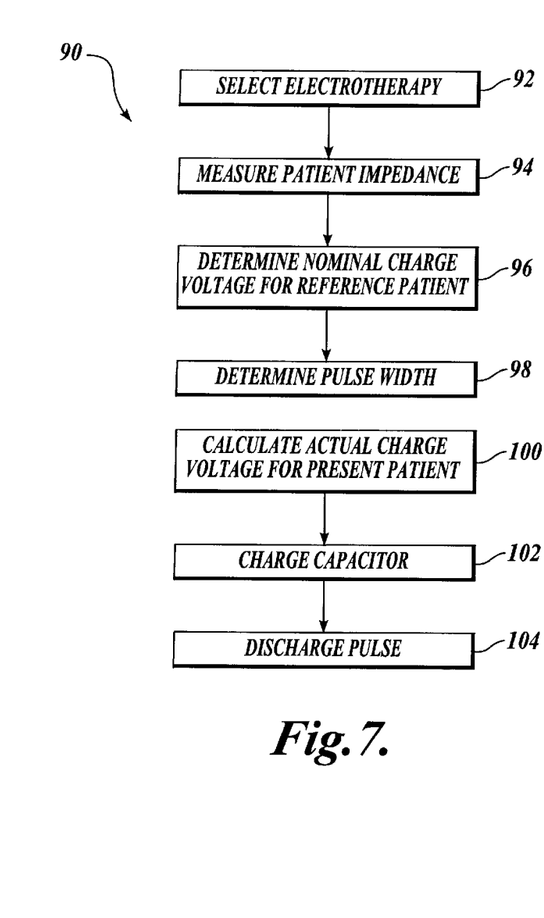
FIG. 7 is a flow chart illustrating an alternative method according to the present invention for controlling the delivery of a defibrillation pulse to produce an equivalent model response in different patients.

It should be understood that the order that actions are taken in the procedure 70 is not critical to the present invention. For example, FIG. 7 provides an alternative procedure 90 for the ongoing operation of the defibrillator 10, with similar-worded actions generally being performed as described in regard to FIG. 6. In the procedure 90, the operator of the defibrillator 10 selects the level of electrotherapy to be provided to the patient (block 92), after which the defibrillator measures the patient's impedance (block 94). Using the operator-selected level of electrotherapy, the defibrillator determines the nominal charge voltage for the reference patient (block 96). The defibrillator also determines an appropriate pulse width for the defibrillation pulse (block 98) using the measured patient impedance. In the procedure 90, the defibrillation pulse width is determined prior to discharging the defibrillation pulse. A predetermined pulse width, in this regard, may be calculated using Equation (8) as set forth above.

Similar to the procedure 70 in FIG. 6, the procedure 90 determines an actual charge voltage for the present patient (block 100) using the measured patient impedance and a predetermined translation factor. The defibrillator then charges its capacitor to the actual charge voltage (block 102), after which it proceeds to discharge the defibrillation pulse (block 104). Regardless of the order in which actions are taken, it is expected that, when implementing the present invention, the actual electrotherapy delivered to a present patient will have the same or substantially similar (e.g., plus or minus a few percentage points) probability of success as the nominal electrotherapy would have for the reference patient. Preferably, this is accomplished by producing a model response in the present patient that is equivalent to the model response expected in the reference patient.

An alternative embodiment of the invention provides electrotherapy resulting in an equivalent probability of success through empirical analysis performed in the preprocessing stage. Rather than preparing an explicit quantitative model for assessing a patient's response, data collected from electrotherapy delivered to a population of patients may be used to assess a model (successful) electrotherapy for a reference patient and the adjustment that must be made to that electrotherapy to deliver an electrotherapy to a different patient with the same probability of success. The adjustment may be expressed in terms of a continuous equation that interpolates between different patients, and the successful electrotherapy for each, to provide electrotherapy to a present patient having an equivalent probability of success. Alternatively, the adjustment may simply be implicit in a table of capacitor charge values (or other electrical parameter that determines the electrotherapy), that relates the actual electrotherapy with the desired probability of success for different patients.

The foregoing description of various embodiments of the invention is not intended to be exhaustive or to limit the invention to the precise forms disclosed. While specific embodiments and examples of the invention are described herein for illustrative purposes, those skilled in the relevant art will recognize various equivalent modifications are possible within the scope of the invention. For example, certain embodiments of the invention discussed above use a translation factor determined beforehand in a preprocessing stage. In other embodiments of the invention, the translation factor may be determined during the ongoing operation of the electrotherapy device. After measuring the patient's impedance, the electrotherapy device may perform calculations that assess the expected model response of the present patient to the nominal electrotherapy and compare the model response of the present patient with the predetermined model response for the reference patient. An appropriate translation factor determined at that time may then be used to adjust the nominal electrotherapy to an actual electrotherapy so that the actual electrotherapy evokes a model response in the present patient that is equivalent to the predetermined response of the reference patient to the nominal electrotherapy.

Moreover, it should be noted that a determination of model response, for purposes of the present invention, is not limited to an assessment of the voltage that develops across a model myocardial cell (e.g., as shown in FIG. 3). More broadly, any suitable model may be used that describes the delivery of a defibrillation pulse to a patient. For example, the earlier-referenced article by Kroll describes the delivery of "effective current" $I_{eff}$ to a patient. In accordance with the present invention, a suitable adjustment, or translation factor, may be determined for adjusting the electrotherapy so that a present patient receives an effective current $I_{eff}$ that is equivalent to the effective current that would be delivered to a reference patient.

Another suitable model is one in which the amount of charge in a defibrillation pulse (or first phase of a multiphasic pulse) is determined for a reference patient. Thereafter, in accordance with the present invention, the nominal defibrillation therapy is adjusted based on a measured patient-dependent electrical parameter of the present patient so that the actual defibrillation pulse, when delivered to the present patient, carries an equivalent amount of charge as the nominal defibrillation pulse carried for the reference patient. In one embodiment of the invention, the amplitude and first phase duration of a multiphasic pulse is determined based on a measured impedance of the patient so that the amount of charge delivered to the patient in the first phase is equivalent for all patients. Persons skilled in the art will recognize that other models for assessing electrotherapy and patient response thereto exist in the art and may be used in accordance with the principles of the present invention.

It should also be understood that there is a variety of ways to calculate a translation factor, as described in the embodiments of the invention provided above. While Equations (11) and (12) describe the derivation of a variable B for a present patient and a reference patient, with the translation factor being determined from a ratio of the variables $B_{PP}$ and $B_{RP}$, it is equally within the scope of the invention to directly compare the model response $V_M$ (Equation (7)) for a present patient and a reference patient. Given a ratio of the model response $V_M$ for a present patient to the model response $V_M$ for a reference patient over a range of present patients, it is possible to calculate a translation factor that would cause the $V_M(PP)/V_M(RP)$ ratio to be constant.

Further enhancements to the translation factor may be determined from empirical analysis of results obtained from implementing the invention with a population of patients. While the translation factor in Equation (13) above is expected to produce an equivalent model response in all of the patients, a test conducted by the assignee of the present invention found that, in an actual implementation, there may be slight, though statistically insignificant, variations in the resulting probability of success across different patients. Empirical data may thus suggest slight modification to the translation factor to maintain an equivalent probability of success for different patients. Based on the results of the above-reference test, the translation factor (for a reference impedance of 50 ohms) may be modified to be:

$$TF = 0.0070 R_L + 0.650 \quad (16)$$

In an alternative embodiment of the invention that uses a reference patient impedance of 80 ohms, the translation factor TF may be modified to be $TF=0.01058 R_L+0.539$. While modifying the translation factor based on empirical data may introduce slight variations in the theoretical model response of different patients, the modification may be advantageous to ensure that the electrotherapy provided by the present invention has an equivalent probability of success in all patients.

The embodiments of the invention in which an exclusive property or privilege is claimed are defined as follows:

1. A medical device for delivering electrotherapy comprising:
   (a) electrodes adapted to be placed on a patient;
   (b) a measuring unit in communication with the electrodes for measuring a patient-dependent electrical parameter of the patient;
   (c) an electrotherapy generator in communication with the electrodes for delivering electrotherapy to the patient;
   (d) a processing unit in communication with the measuring unit and the electrotherapy generator for controlling the electrotherapy that is delivered to the patient, wherein the processing unit is configured to cause the electrotherapy generator to deliver an electrotherapy that is adjusted for the patient based on the patient's measured patient-dependent electrical parameter, the electrotherapy being adjusted in accordance with the measured patient-dependent electrical parameter to have an equivalent probability of success in substantially all patients.

2. The medical device of claim 1, wherein the patient-dependent electrical parameter is impedance.

3. The medical device of claim 2, wherein the impedance is transthoracic impedance.

4. The medical device of claim 1, wherein the patient is a present patient, and wherein the electrotherapy for the present patient is adjusted from a nominal electrotherapy, the adjustment using the present patient's measured patient-dependent electrical parameter and a predetermined response of a reference patient to the nominal electrotherapy to produce electrotherapy for the present patient having a probability of success equivalent to the probability of success of the nominal electrotherapy for the reference patient.

5. The medical device of claim 4, wherein the predetermined response of the reference patient is based on a quantitative model, and wherein the electrotherapy for the present patient produces a model response in the present patient that is equivalent to the predetermined model response of the reference patient to the nominal electrotherapy.

6. The medical device of claim 4, wherein the adjustment is derived from a predetermined translation factor that, when applied to the nominal electrotherapy, translates the nominal electrotherapy to the electrotherapy for the present patient.

7. The medical device of claim 6, wherein the predetermined translation factor is derived from:
   (a) comparing the predetermined model response of the reference patient to the nominal electrotherapy with the model response of a range of different patients to the nominal electrotherapy; and
   (b) compensating for relative differences in model response between the reference patient and the different patients so that the translation factor, when applied to the nominal electrotherapy, results in electrotherapy that produces an equivalent model response in the different patients.

8. The medical device of claim 1, wherein the electrotherapy generator includes an energy storage device from which the electrotherapy is delivered to the patient, and wherein the electrotherapy for the patient is adjusted by adjusting the charge level to which the energy storage device is charged.

9. The medical device of claim 8, wherein the adjustment to the charge level of the energy storage device is made after charging the energy-storing device has commenced.

10. A method of delivering electrotherapy, comprising:
    (a) selecting a nominal electrotherapy for a present patient;
    (b) determining the response of a reference patient to the nominal electrotherapy, the reference patient having a patient-dependent electrical parameter of a reference amount;
    (c) measuring a patient-dependent electrical parameter in the present patient that corresponds to the reference patient-dependent electrical parameter; and
    (d) controlling the delivery of electrotherapy to the present patient based on the present patient's measured patient-dependent electrical parameter and the determined response of the reference patient to produce an actual electrotherapy that, when delivered to the present patient, has a probability of success for the present patient that is equivalent to the probability of success of the nominal electrotherapy for the reference patient.

11. The method of claim 10, further comprising storing an electrical charge in a capacitor and connecting the capacitor to the present patient to deliver the actual electrotherapy, wherein the delivery of the actual electrotherapy to the present patient is controlled by controlling the charge level to which the capacitor is charged.

12. The method of claim 11, further comprising:
    (a) commencing to charge the capacitor to a nominal charge level designed for delivering the nominal electrotherapy to the reference patient; and
    (b) adjusting the charge level of the capacitor from the nominal charge level to an actual charge level based on the measured patient-dependent electrical parameter of the present patient.

13. The method of claim 10, wherein the patient-dependent electrical parameter of the reference patient and the corresponding patient-dependent electrical parameter of the present patient is impedance.

14. The method of claim 13, wherein the impedance is transthoracic impedance.

15. The method of claim 10, wherein the determined response of the reference patient is based on a quantitative model, and wherein the actual electrotherapy to be delivered to the present patient is controlled to produce a model response in the present patient that is equivalent to the determined model response of the reference patient to the nominal electrotherapy.

16. The method of claim 15, further comprising:
(a) using the quantitative model, determining a model response of a range of different patients to the nominal electrotherapy, the different patients having a corresponding patient-dependent electrical parameter of an amount different than the reference amount of the reference patient;
(b) comparing the determined model response of the reference patient to the determined model response of the range of different patients; and
(c) determining a translation factor that compensates for relative differences in model response between the reference patient and the different patients to the nominal electrotherapy, so that when applied to the nominal electrotherapy, the translation factor translates the nominal electrotherapy to actual electrotherapy that produces an equivalent model response in the different patients.

17. The method of claim 16, wherein the translation factor uses the measured patient-dependent electrical parameter of the present patient to define an adjustment that is applied to the nominal electrotherapy to produce the actual electrotherapy for the present patient.

18. A medical device for delivering electrotherapy, comprising:
(a) electrodes adapted to be placed on a present patient;
(b) an impedance measuring unit in communication with the electrodes for measuring an impedance of the present patient;
(c) an electrotherapy generator in communication with the electrodes for delivering electrotherapy to the present patient; and
(d) a processing unit in communication with the impedance measuring unit and the electrotherapy generator for controlling the electrotherapy that is delivered to the present patient, wherein the processing unit is configured to cause the electrotherapy generator to deliver an actual electrotherapy to the present patient based on the present patient's measured impedance and a predetermined response of a reference patient to a nominal electrotherapy, the processing unit controlling the electrotherapy generator so that the actual electrotherapy delivered to the present patient has a probability of success for the present patient that is equivalent to the probability of success of the nominal electrotherapy for the reference patient.

19. The medical device of claim 18, wherein the medical device is a defibrillator and the electrotherapy delivered from the electrotherapy generator is a defibrillation pulse.

20. The medical device of claim 18, wherein the electrotherapy generator includes a capacitor for storing a charge from which the electrotherapy is produced, and wherein the processing unit controls the electrotherapy by controlling the charge level to which the capacitor is charged.

21. The medical device of claim 20, wherein the electrotherapy generator commences charging the capacitor to a nominal charge level designed for the nominal electrotherapy and after measuring the present patient's impedance, adjusts the charge level of the capacitor to produce the actual electrotherapy.

22. The medical device of claim 18, wherein the predetermined response of the reference patient is based on a quantitative model, and wherein the actual electrotherapy is designed to produce a model response in the present patient that is equivalent to the predetermined response of the reference patient to the nominal electrotherapy.

23. The medical device of claim 22, wherein the processing unit uses a translation factor to control the actual electrotherapy that is delivered to the present patient, the translation factor translating the nominal electrotherapy designed for the reference patient to the actual electrotherapy designed for the present patient.

24. The medical device of claim 23, wherein the translation factor uses the present patient's measured impedance to define an adjustment that is applied to the nominal electrotherapy to produce the actual electrotherapy.

25. The medical device of claim 23, wherein the translation factor is derived by:
(a) comparing the predetermined response of the reference patient to the nominal electrotherapy with the model response of a range of different impedance patients to the nominal electrotherapy; and
(b) determining an adjustment that compensates for relative differences in model response between the reference patient and the different impedance patients so that the adjustment, when applied to the nominal electrotherapy, results in an actual electrotherapy that produces an equivalent model response in the different impedance patients.

26. A method of determining a translation factor for use in an electrotherapy device that produces electrotherapy for different patients having an equivalent probability of success for the different patients, the method comprising:
(a) preparing a quantitative model of an electrotherapy device/patient system defined by the electrotherapy device attached to a patient, the quantitative model including a patient-dependent electrical parameter for the patient;
(b) selecting a nominal electrotherapy;
(c) using the quantitative model, determining the model response of a reference patient in the electrotherapy device/patient system to the nominal electrotherapy, the patient-dependent electrical parameter for the reference patient having a reference amount;
(d) using the quantitative model, determining the model response of different patients in the electrotherapy device/patient system to the nominal electrotherapy, the patient-dependent electrical parameter for the different patients having amounts different than the reference amount;
(e) comparing the model response of the reference patient with the model response of the different patients to the nominal electrotherapy; and
(f) determining the translation factor to provide an adjustment for the different patients that compensates for relative differences between the model response of the reference patient and the model response of the different patients to the nominal electrotherapy, the adjustment modifying the nominal electrotherapy to define an actual electrotherapy that, when delivered to a patient, produces a model response in the patient that is equivalent to the model response of the reference patient to the nominal electrotherapy.

27. The method of claim 26, wherein the translation factor is an equation that uses a measured patient-dependent electrical parameter of a present patient to define the adjustment that modifies the nominal electrotherapy to produce the actual electrotherapy for the present patient.

28. The method of claim 26, wherein the patient-dependent electrical parameter is impedance.

29. The method of claim 28, wherein the impedance is transthoracic impedance.

30. A defibrillator comprising:

(a) electrodes adapted for placement on a patient;

(b) a measuring unit in communication with the electrodes for measuring a patient-dependent electrical parameter of the patient;

(c) an electrotherapy generator in communication with the electrodes for delivering multiphasic defibrillation therapy to the patient; and (d) a processing unit in communication with the measuring unit and the electrotherapy generator for controlling the defibrillation therapy that is delivered to the patient, wherein the processing unit is configured to cause the electrotherapy generator to deliver multiphasic defibrillation therapy having an amplitude and phase duration that are determined based on the measured patient-dependent electrical parameter to produce defibrillation therapy having an equivalent probability of success for the patient as for other patients, the defibrillation therapy delivering an amount of energy to the patient that is increased or decreased in relation to a corresponding increase or decrease of the measured patient-dependent electrical parameter of the patient.

31. The defibrillator of claim 30, wherein the patient-dependent electrical parameter is impedance, and wherein the amount of energy delivered to the patient is increased if the patient's measured impedance is higher than a nominal reference impedance, and the amount of energy delivered is decreased if the patient's measured impedance is lower than the nominal reference impedance.

32. The defibrillator of claim 30, wherein the electrotherapy generator includes a capacitor for storing a charge from which the defibrillation therapy is produced, and wherein the processing unit controls the amplitude of the multiphasic defibrillation therapy by controlling the charge level to which the capacitor is charged.

33. The defibrillator of claim 32, wherein the capacitor is charged to an actual charge level determined using the measured patient-dependent electrical parameter to calculate an adjustment that, when applied to a nominal charge level, translates the nominal charge level to the actual charge level.

34. The defibrillator of claim 33, wherein the actual charge level causes the capacitor, upon discharge, to deliver defibrillation therapy that produces in the patient a model response that is equivalent to the model response of a reference patient to defibrillation therapy produced from charging the capacitor to the nominal charge level.

35. The defibrillator of claim 30, wherein the phase duration is determined prior to delivery of the defibrillation therapy to minimize the leading edge voltage of the defibrillation therapy for successful defibrillation.

36. The defibrillator of claim 30, wherein the phase duration is determined during delivery of the defibrillation therapy based on a patient-dependent parameter observed during the defibrillation therapy.

37. The defibrillator of claim 30, wherein the defibrillation therapy delivers to the patient an initial defibrillation current that, relative to the initial defibrillation current that would be delivered to a reference patient of 80 ohms, is approximately 45% higher for a 40 ohm patient, 15% higher for a 60 ohm patient, 7% lower for a 100 ohm patient, and 16% lower for a 120 ohm patient.

38. The defibrillator of claim 30, wherein the processing unit controls the amplitude and phase duration of the first phase of the multiphasic defibrillation therapy to deliver to the patient an amount of charge in the first phase that is equivalent for all patients.

* * * * *